US005789190A

United States Patent [19]

Crabb et al.

[11] Patent Number: 5,789,190
[45] Date of Patent: Aug. 4, 1998

[54] METHODS AND KIT FOR THE DETECTION OF CRYPTOSPORIDIUM OOCYSTS AND GIARDIA CYSTS

[75] Inventors: Joseph H. Crabb, Newfield; Nathan B. Turner, Portland, both of Me.

[73] Assignee: ImmuCell Corporation, Portland, Me.

[21] Appl. No.: 727,885

[22] Filed: Oct. 9, 1996

[51] Int. Cl.$^6$ .............................. B01D 21/00; C12N 1/22; C12N 1/20; C12Q 1/04
[52] U.S. Cl. ......................... 435/34; 210/600; 210/601; 210/610; 210/615; 210/767; 210/800; 435/261
[58] Field of Search ..................... 210/600, 601, 210/610, 615, 767, 800; 435/261, 34

[56] References Cited

U.S. PATENT DOCUMENTS 4,876,013  10/1989  Shmidt et al. ........................ 210/650

OTHER PUBLICATIONS

Bifulco et al., "Antibody–Magnetite Method for Selective Concentration of Giardia Iamblia Cysts from Water Samples", *Applied and Environmental Microbiology*, 772–776 (1993).

LeChevallier et al., "Evaluation of the Immunofluorescence Procedure for Detection of Giardia Cysts and Cryptosporidium Oocysts in Water", Applied and Environmental Microbiology, 690–697 (1995).

LeChevallier et al., "Occurrence of Giardia and Cryptosporidium spp. in Surface Water Supplies", *Applied and Environmental Microbiology*, 2610–2616 (1991).

Vesey et al., "Routine monitoring of Cryptosporidium oocysts in water using flow cytometry", Journal of Applied Bacteriology, 87–90 (1993).

Musical et al., "Detection of Cryptosporidium in Water by Using Polypropylene Cartridge Filters", Applied and Enviromental Microbiology, 687–692 (1987).

Vesey et al., "A new method for the concentration of Cryptosporidium oocysts from water", Journal of Applied Bacteriology, 82–86 (1993).

Tsai et al., "Simple method of concentrating enteroviruses and hepatitis A virus from sewage and ocean water for rapid detection by reverse transcriptase–polymerase chain reaction", *Appl. Environ, Microbiol.* 59(10): 3488–91 (1993).

Tsai et al., "Detection of poliovirus, hepatitis A virus, and rotavirus from sewage and ocean water by triplex reverse transcriptase PCR", *App. Environ. Microbiol.* 60(7): 2400–7 (1994).

Paul et al., "Concentration of viruses and dissolved DNA from aquatic environments by vortex flow filtration", *Appl. Environ. Microbiol.* 57(8): 2197–204 (1991).

Bellhouse et al., "A high efficiency membrane separator for donor plasmapheresis", *Asaio Trans.* 34(3): 747–54 (1988).

Ohashi et al., "Rotation–induced Taylor vortex enhances filtrate flux in plasma separation", *Asaio Trans.* 34(3): 300–7 (1988).

*Primary Examiner*—David M. Naff
*Assistant Examiner*—Deborah K. Ware
*Attorney, Agent, or Firm*—Kevin M. Farrell

[57] ABSTRACT

Disclosed are methods and kits for the detection of Cryptosporidium oocysts and Giardia cysts. Such methods include the concentration of a water sample to form a retentate followed by resolution the retentate by density centrifugation. At least one layer is formed which retains the microbes to be detected. The presence of microbes within resolved layers is then detected.

8 Claims, 1 Drawing Sheet

METHODS AND KIT FOR THE DETECTION OF CRYPTOSPORIDIUM OOCYSTS AND GIARDIA CYSTS

FIELD OF THE INVENTION

This invention relates to methods and articles of manufacture for the detection of Giardia cysts and Cryptosporidium oocysts in water.

BACKGROUND OF THE INVENTION

Giardia cysts and Cryiptosporidium oocysts are protozoan intestinal parasites. As used herein "Giardia" refers to a genus of flagellates that parasitize the small intestine of mammals. One species of Giardia of particular significance, G. Lamblia, has eight flagella and a flattened heart-shaped appearance under microscope. The organism attaches itself to the intestinal mucosa by sucking organs.

As used herein, "Cryptosporidium" refers to a genus of coccidian sporozoan, which are opportunistic parasites in mammals. Cryptosporidiosis, in immunocompetent individuals, is self-limiting. In immunocompromised individuals, it may be fatal.

Outbreaks of giardiasis and cryptosporidiosis are typically caused by contamination of water supplies. These water borne organisms are difficult to detect. Presently, seven Giardia cysts per 100 L of water is considered potable. To evaluate water supplies one must be able to reliably and reproducibly detect such a level of Giardia, at a reasonable cost Although no acceptable level of Cryptosporidium oocysts in water supplies has been defined, such definition is expected in the near future. The level of Cryptosporidium oocysts in water supplies, like Giardia, will be a small, limited number.

Present technology does not presently permit the detection of Giardia cysts or Cryptosporidium oocysts from water supplies in a sensitive, reproducible manner at a reasonable cost. Giardia and Cryptosporidium are presently detected using cartridge filters for concentrating organisms from large volumes of water, processing the filters by mechanical disruption, collecting the oocysts via density gradient centrifugation and standard centrifugation, and detection via immunofluorescence assay (IFA). This method is time consuming, labor intensive and requires considerable analytical expertise. The method suffers from a low efficiency in recovering cysts and oocysts from the sample and frequently produces questionable results.

The present invention is directed to methods and articles of manufacture for the detection of Giardia cysts and Cryptosporidium oocysts. The methods are less time consuming, less labor intensive and are more sensitive and reproducible in the recovery of Giardia cysts and Cryptosporidium oocysts than previous methods.

SUMMARY OF THE INVENTION

The present invention features methods and articles of manufacture for the detection of Giardia cysts and Cryptosporidium oocysts in samples. One embodiment of the present invention is a method of detecting the presence or absence in a sample of at least one of the organisms selected from the group consisting of Cryptosporidium and Giardia, which sample is a volume of water potentially containing such organisms.

The term "monitoring" is used in the sense of checking or examining systematically for the presence or absence of Cryptosporidium and/or Giardia.

The term "detecting the presence or absence" is used in the sense of clinically acceptable standards for the presence or absence of Cryptosporidium and Giardia. These acceptable standards are approximately 100 cysts or oocysts per 100 liters of sample, and more preferably, approximately seven cysts per 100 liters of sample for Giardia.

The method comprises the step of concentrating the sample by a factor of $1 \times 10^2$ to $1 \times 10^5$ of the original volume by removing water,to form a retentate. The retentate is then subjected to density gradient centrifugation to form layers potentially containing oocysts and debris. The oocyst-containing layer is diluted and reconcentrated to form a final retentate. The final retentate is then monitored for the presence of the organism.

Preferably, the step of concentrating the sample is performed with a polymeric membrane. A preferred membrane has a molecular weight cutoff of approximately 100–500 kDa. That is, the membrane tends to pass materials smaller than a molecular weight of 100,000 to 500,000 Daltons. This molecular weight cutoff corresponds approximately to a membrane pore size of 0.01–0.05 µm. A preferred molecular weight cutoff is 500,000 Daltons.

Membranes having a molecular weight cutoff less than 100,000 Daltons may be used. However, membranes with a molecular weight cutoff of 10 to 100 kDa concentrate at a very slow rate. Membranes having a pore diameter of greater than 0.05 µm may also be used. However, membranes with a pore diameter of 0.5–2µm may not retain organisms or organisms may enter the pore structure and become trapped, and have a greater tendency to plug or 'blind over'.

Preferably, the step of concentrating the sample uses such membranes capable of generating Taylor vortices. A preferred means for imparting Taylor vortices is with a membrane that is cylindrical or conical. The cylindrical or conical membrane is received in a cylindrical or conical membrane support. The membrane and membrane retaining support are contained in a larger cylindrical or conical vessel having walls. The vessel walls and the membrane define a chamber for containing sample. Sample contacts the membrane with a pressure drop as the membrane and membrane retaining support are rotated with respect to the sample. The rotation of the membrane creates Taylor vortices. A preferred device for generating Taylor vortices is described in U.S. Pat. No. 4,876,013, which patent is incorporated herein by reference.

Preferably, the step of density gradient separation of oocysts and cysts from debris in the concentrate uses cesium chloride. Such density gradients have been described previously:

Kilani RT, Sekla L (1987) Purification of Cryptosporidium oocysts and sporozoites by cesium chloride and percoll gradients. Am. J. Trop. Med. Hyg. 36:505–508 Preferably, cyst or oocyst-containing concentrates, which also contain considerable debris that will ultimately obscure detection, are applied into a centrifuge tube containing a concentration gradient of cesium chloride. The concentration gradient is prepared in a continuous or a discontinuous step-wise manner. This gradient is subjected to centrifugation conditions such that the debris moves through the gradient and sediments in the bottom of the tube; the cysts or oocysts, which are buoyant at the CsCl densities employed, remain suspended in the gradient, and can be recovered by withdrawing the fluid overlaying the debris-containing sediment.

The resulting suspension of cysts and oocysts is then prepared and diluted by the addition of water. This suspension is concentrated by removal of water, and the solutes are exchanged through simultaneous addition and removal of water, until a retentate is formed which is substantially free of CsCl.

The oocysts and cysts retained are preferably indirectly fluorescent-antibody labeled and examined under microscope. However, other means of determining the presence of Giardia cysts and Cryptosporidium oocysts may be used. Such other means include, by way of example, without limitation, automated photo detectors responsive to fluorescent-antibody labeled oocysts or cysts, radio-photographic techniques using radiolabels, enzyme-linked antibody detection systems, nucleic acid probe technology (including polymerase chain reaction).

One embodiment of the present invention features a kit for performing an assay for detecting the presence or absence of at least one of the organisms selected from the group consisting of Cryptosporidium and Giardia, which organism potentially exists in a sample comprising a volume of water. The kit comprises means for reducing the volume of the sample by $1 \times 10^2 - 1 \times 10^5$ to form a retentate. The kit further comprises means for forming a density gradient. Following the formation of a retentate, the retentate is exposed to density gradient centrifugation, dilution and re-concentration. Finally, the processed sample is examined by direct or indirect immunofluorescence.

Preferably, the kit comprises a membrane for forming the retentate. A preferred membrane is capable of filtration through the generation of Taylor Vortices. Preferably the membrane has a molecular weight cutoff of 100,000–500,000 Daltons. This molecular weight cutoff corresponds approximately to a pore size of 0.01–0.05 μm.

Preferably, the kit comprises means for performing density gradient centrifugations, such as solutions of cesium chloride, diluent buffers, and the like.

Preferably, the kit comprises means for indirectly fluorescently labeling Giardia cysts and Cryptosporidium oocysts to allow examination under microscope, such as monoclonal antibodies, fluorescently labeled supplementary reagents, diluents, and the like.

Surprisingly, and unexpectedly, embodiments of the present invention are capable of recovering approximately 50–70% of Cryptosporidium oocysts present in samples. Samples may range in size from 10–500 L of water and be of vastly different quality. These high levels of recovery are not attained with methods employing cartridge filters. Methods employing cartridge filters have a low efficiency of detection of cysts and oocysts, typically <10%.

These and other advantages will be apparent from the drawings and the detailed description which follows.

DETAILED DESCRIPTION OF THE INVENTION

Figure 1:
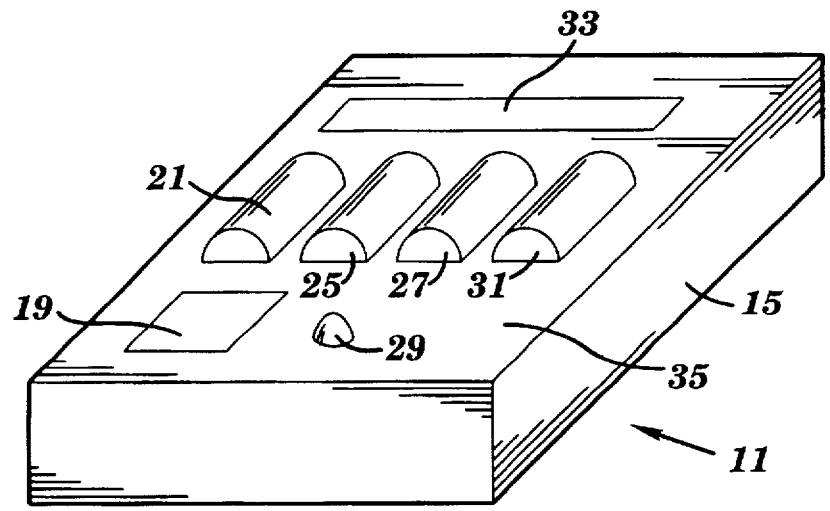
FIG. 1 depicts a kit embodying features of the present invention.

The present invention is directed to methods of detecting Giardia cysts and Cryptosporidium oocysts and articles of manufacture to perform such methods. The methods and articles of manufacture are described with respect to membranes which use Taylor vortices as a preferred embodiment. However, other means of concentrating a sample which do not cause disruption of the cyst or oocyst and have similar efficiencies can be substituted for methods and apparatus which utilize Taylor vortices.

The present invention will be described with respect to a kit, generally designated by the numeral 11. Kit 11 has the following major elements: package 15, membrane 19, density gradient medium vial 21, a first diluent buffer vial 25, a second diluent buffer vial 27, labeling antibody vial 29, immunofluorescent reagent vial 31, and instructions 33.

Package 15 is a box or other suitable means for holding membrane 19, density gradient medium vial 21, first diluent buffer vial 25, second diluent buffer vial 27, labeling antibody vial 29, immunofluorescent reagent vial 31, and instructions 33.

Package 15 may take many different forms and shapes. As depicted in Fig. 1, Package 15 is a rectangular box with an expanded foam insert 35 to cushion and insulate the vials contained therein.

Membrane 19 is preferably comprised of hydrophilic polymeric composition. The membrane has pores with a molecular weight cutoff of 100,000–500,000 Daltons and most preferably, about 500,000 Daltons. This molecular weight cut off corresponds approximately to a pore size of 0.01–0.05 μm.

Membrane 19 is capable of assuming a cylindrical shape. Preferably, membrane 19 is capable of being received in a vortex flow filtration assembly, generally described in FIG. 2. A detailed description of vortex flow assemblies is provided in U.S. Pat. No. 4,876,013 to Schmidt et al., which reference is incorporated herein.

Figure 2:
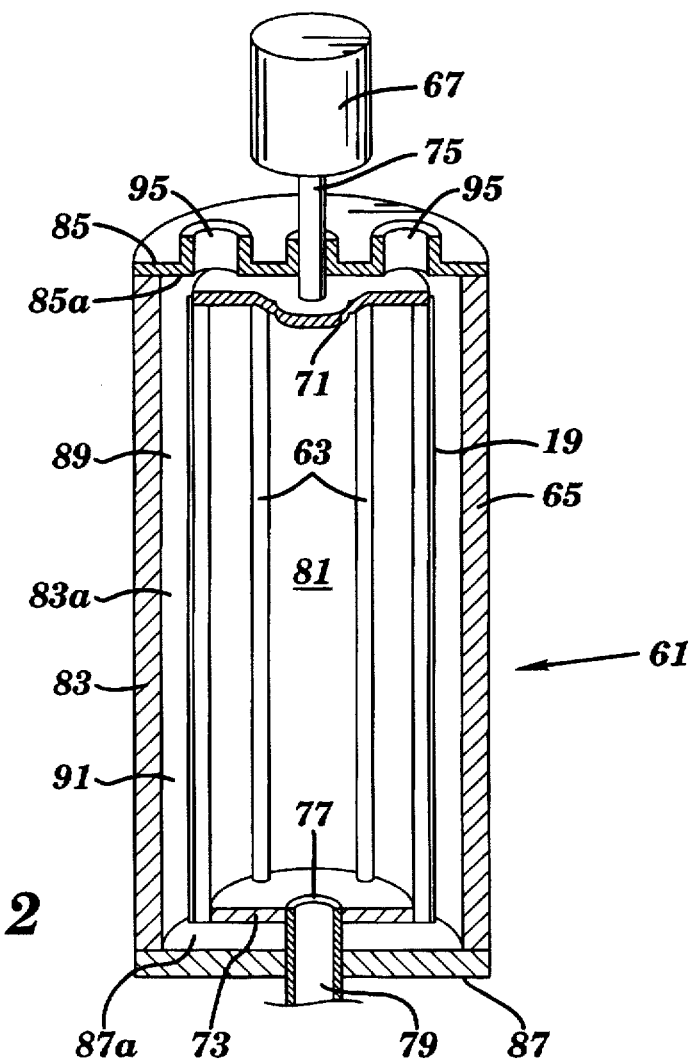
FIG. 2 depicts a vortex flow membrane device.

Turning now to FIG. 2, a vortex flow assembly generally designated by the numeral 61 comprises the following major elements: a membrane support 63, a stationary vessel 65, and motor 67. Membrane 19 is held on rotatable membrane support 63.

Membrane 19 may be cylindrical or may be a sheet of porous polymeric material which can be rolled and secured by suitable clips adhesive or welds (not shown) in the shape of a cylinder surrounding the membrane support 63. Membrane support 63 has a top end 71 and a bottom end 73. Top end 71 is mechanically linked to motor 67 by a shaft 75. Bottom end 73 has an axial opening 77 which rotatably receives a hollow shaft 79.

Membrane 19 and membrane support 63 define an inner chamber 81 "for receiving fluids drawn or permeated through membrane 19. Fluid in inner chamber 81 is removed by hollow shaft 79.

Stationary vessel 65 has the following major elements: a cylinder housing 83, a top housing 85, and a bottom housing 87. Cylinder housing 83 has cylindrical walls 83a defining an open cylinder having a top and a bottom. Top housing 85 is received at the top of cylindrical housing 83. Bottom housing 87 is received at the bottom of the cylinder housing 83. Bottom housing 87 and top housing 85 have substantially planar surfaces 87a and 85a, respectively, which with cylindrical walls 83a define a cylinder chamber 89. Cylinder chamber 89 is capable of receiving membrane 19 and membrane support 63. The area 91 between cylindrical wall 83 and membrane 19 of stationary chamber 89 is for receiving sample.

Top housing 85 has an opening 95 in communication with area 91 for receiving sample and an opening 97 for supplying pressure, if desired. Top housing 85 rotatably receives shaft 75. Bottom housing 87 receives hollow shaft 79 to allow inner chamber 81 to be placed in fluid communication with a vacuum source or to drain inner chamber 81.

Preferably, bottom housing 87 and/or top housing 85 are removable from cylinder housing 83 to allow servicing of the membrane.

Sample is received in area 91 of cylinder chamber 89. As membrane 19 is rotated on shaft 75 by motor 67, Taylor vortexes are generated in area 91 which sweep the membrane and prevent occlusion. Retentate is maintained in area 91. Filtrate enters inner chamber 81 and is removed via hollow shaft 79. Samples are reduced in volume by $1\times10^2$ to $1\times10^5$ using the vortex flow assembly 61.

Returning now to FIG. 1, density gradient medium vial 21 contains cesium chloride solution. In the alternative, Vial 21 contains dry cesium chloride powder for reconstitution. In the event vial 21 contains dry powder, the kit further comprises vials (not shown) containing appropriate diluents and solutions for reconstitution. Such diluents and solutions are known to individuals skilled in the art.

The density gradient medium of vial 21 is capable of separating Cryptosporidium oocysts and Giardia cysts from debris found in the sample concentrates. A suitable volume of density gradient medium is added to the retentate to achieve a cesium chloride density of 0.5 g/ml. Density gradient medium is further diluted with diluent contained in diluent buffer held in the first diluent buffer vial 25 in order to achieve three cesium chloride concentrations in separate tubes; 1.4 g/ml, 1.1 g/ml, and 1.05 g/ml respectively.

These solutions of cesium chloride are aliquotted into a single tube, or in several tubes to form a gradient from the highest density in the bottom to the lowest density on the top, such that each tube contains 7.5 ml of each of the solutions. To each of these tubes, 2–5 ml of the retentate is carefully layered on the top of the gradient, such that it floats on top of the gradient. These tubes are centrifuged in a swinging bucket rotor for 1 hour at 16,000 ×g in order to separate the debris from the organisms contained in the retentate.

The central layer of the gradient is removed using a pipette, diluted with water to 50–100 ml to form a first dilution. Returning now to FIG. 2 the dilution is dispensed back into the vortex flow assembly 61. This sample is re-concentrated, as described previously with respect to the initial sample to form a first concentrate.

The first concentrate in the concentration chamber 89 is diluted with water to form a second dilution and the second dilution is reconcentrated to form a second concentrate. The result of this diafiltratrion step is to reduce the amount of residual cesium chloride in the retentate, to facilitate subsequent immunofluorescent labeling.

Immunofluorescence reagent vial 31 contains immunofluorescent reagent to indirectly label the organism. Second diluent buffer vial 27 and labeling antibody vial 29 are additional reagents and diluents required to conduct the immunofluorescent labeling. If the immunofluorescent labeling is a direct labeling, or if comprised of a plurality of components, may be contained in fewer, or additional vials (not shown). Instructions 33 describes the methods and procedures to detect Giardia cysts and Cryptosporidium oocysts. The instructions are summarized in the following discussion of the operation of the assay.

In operation, membrane 19 is removed from kit 11 and placed upon a membrane support 63. The membrane is comprised of a hydrophilic polymer of 500,000 Da molecular weight cut off, corresponding to a 0.05 micrometer pore size. The membrane has a transmembrane flux rate of approximately 40 to 115 milliliters per minute. Membrane support 63 and membrane 19 are placed within cylindrical housing 83. Membrane support 63 is mechanically linked to motor 67 by shaft 75. The top housing 83 and bottom housing 87 are affixed to the end of cylindrical cylinder housing 83.

A sample of approximately 10–500 L is received through opening 95 and into the area 91 between cylindrical wall 83 and membrane 19. A small pressure of <15 psi is exerted in the area 91 by the incoming sample and additional pressure can be asserted through opening 97 if desired.

As membrane 19 is rotated on shaft 75 by motor 67, Taylor vortexes are generated which sweep the membrane 19 and prevent occlusion. The membrane rotational speed is approximately 2,000 to 4,000 revolutions per minute.

The filtrate enters inner chamber 81 and is removed via hollow shaft 79. A negative pressure of minus 5 to minus 12 pounds per square inch is exerted through the shaft opening 75. The retentate is removed from area 91 by pouring such retentate from opening 95 or removing the top housing 83. The retentate constitutes 5 to 250 ml of an original 10 to 500 L sample, a reduction in volume of $1\times10^2$ to $1\times10^5$.

The retentate, having a volume of approximately 5 to 15 ml is separated from the membrane 19 and the vortex flow assembly 61 by pouring such retentate from opening 95 or removing the top housing 83. The retentate is placed in a suitable containment vessel such as a test tube.

The density gradient medium of vial 21 is added to the retentate to achieve a cesium chloride density of 0.5 g/ml. Density gradient medium is further diluted with diluent contained in first diluent buffer vial 25 in order to achieve three cesium chloride concentrations in separate tubes; 1.4 g/ml, 1.1 g/ml, and 1.05 g/ml respectively.

These solutions of cesium chloride are combined into a single tube, or in several tubes (depending on the volume of retentate to be separated) to form gradients from the highest density in the bottom to the lowest density on the top, such that each tube contains 7.5 ml of each of the solutions. To each of these tubes, 2–5 ml of the retentate is carefully layered on the top of the gradient, such that it floats on top of the gradient. These tubes are centrifuged in a swinging bucket rotor for 1 hour at 16,000×g in order to form layers of debris and one or more layers potentially containing the organisms.

The central layer of the gradient potentially containing the organisms is removed using a pipette and diluted with water to 50–100 ml to form a first dilution. This first dilution is dispensed back into the vortex flow assembly 61. This first dilution is re-concentrated as previously described to form a first concentrate.

The concentration chamber 89 is filled with water to form a second dilution. The second dilution is reconcentrated to form a second concentrate. The result of this diafiltratrion step is to reduce the amount of residual cesium chloride in the retentate, to facilitate subsequent immunofluorescent labeling.

The second concentrate, the final retentate, is removed from the chamber. The final retentate is centrifuged at 2000×g for 15 minutes to sediment the oocysts and cysts. The organisms are resuspended in a solution of 50–200 uL of water and, more preferably, 75–125 uL of water. Immunofluorescent reagents comprising a labeled antibody or combination of antibodies and labeled antibodies capable of forming a complex with the cysts or oocysts are removed from labeling antibody vial 29 and immunofluorescent reagent vial 31 and combined with the neutralized sample. The immunofluorescent reagents are allowed to incubate for 10 to 60 minutes. The cysts or oocysts, if present, are then available for examination under microscope.

The organisms may be detected by DNA and RNA analysis. Suitable probes would be isolated from genomic DNA, messenger RNA and/or ribosomal RNA. Techniques for performing polymerase chain reaction (PCR) analysis and nucleic acid hybridization analysis are known in the art.

The present method and articles of manufacture provide for reliable, and cost effective detection of Giardia cysts and Cryptosporidium oocysts. These and other advantages will be further described with respect to the following examples.

EXAMPLE 1

The following example features the isolation and examination of Cryptosporidium oocysts. The isolation and examination of Giardia cysts would be similar, however, antibody compositions for Giardia cysts would be substituted for antibodies for Cryptosporidium oocysts.

Monoclonal antibodies directed to Cryptosporidium oocysts or Giardia cysts (immunofluorescent reagent) are developed in the following manner. Balb/CJ or RBN/df (Jackson Laboratories, Bar Harbor, Me.) mice are immunized intraperitoneally, with oocysts or cysts which have been purified and formalin fixed in 10% formalin, or alternatively, oocyst walls isolated by excystation and differential centrifugation separating sporozoites from oocyst walls. These antigens would be emulsified in Complete Freund's Adjuvant (Difco, Detroit Mi.). The immunization is repeated several times. The final immunization is administered intravenously. Four to six days after the final immunization the animals are sacrificed. The spleen is aseptically removed and placed in a petri dish with 5 ml cell culture media. The spleens are rinsed in sterile media then transferred to a new petri dish containing 5 ml media. The spleen cells are released from the tissue using sterile forceps and 60/80 mesh stainless steel screen. The released cells are transferred to a conical vessel and allowed to settle. The supernatant is poured off and the remaining cells and liquid are centrifuged (400×g) for fifteen minutes. The cells are resuspended in 0.5 ml fetal calf serum (FCS). To the resuspended cells, 4.5 ml red blood cell lysis buffer (10, mM Tris pH 7.2, 144, mM $NH_4C$ 1) is added. The resuspended cells are allowed to incubate in red blood cell lysis buffer for five minutes. After incubation, 10 ml of cold media with FCS (2.5%) is added to the resuspended cells. The cells are again spun at 400×g for five minutes. The cells are then resuspended in 25 ml media.

Myeloma cells for fusion to splenocytes are prepared with SP2/0 cells (ATCC, Rockville, Md.). These cells are thawed, grown in cell culture media and prepared at a concentration of $1 \times 10^7$ cells per ml.

Splenocytes and myeloma cells are combined in a ratio of three splenocytes cells to one myeloma cell. The mixture of cells is spun at 400×g for five minutes and the cells resuspended in 25 ml of media with no serum. The resuspended cells are spun at 400×g for ten minutes and the supernatant removed.

The pellet is tapped to resuspend and the test tube containing the pellet is placed in a water bath of 37° C. To the pellet 1 ml of 50% polyethyleneglycol (PEG 1,500–3,000 mw)/media at 37° C. is added dropwise over one minute(~1 drop every 3 sec.). This mixture is gently stirred with the pipette tip during and for up to one minute after the addition.

Next, 1 ml of media/no serum at 37° C. is added over a one minute period with stirring. This step is repeated, and followed with the addition of 2 ml media/no serum at 37° C. over a one minute period. Next, 7 ml of media/2.5% FCS at 37° C. is added over 2 minutes while swirling the tube, to dilute out the PEG. This mixture is spun, at 400×g for 5 minutes, and the supernatant is aspirated. The cells are then resuspended in 10 ml of media/10% FCS medium at 37° C. by shooting media at the pellet and stirring. The concentration of the cell mixture is adjusted to approximately $1 \times 10^7$ cells per ml by gently swirling the cells in the tube.

These cells are plated in 96 well tissue culture dishes at $1 \times 10^6$ cells per well. Cells are maintained with the addition of 0.1 ml 1×hypoxanthine aminopterine/thymidine (HAT) to each well the day following plating. On the fifth, seventh and ninth day following plating, 0.1 ml of fluid is removed from each well and replaced with 0.1 ml×HAT. This process is repeated every 3–4 days thereafter. After 1–3 weeks hybrid cells are observed as small clusters. Hybridomas secreting antibodies of the desired specificity are detected by performing indirect immunofluorescence microscopy using the hybridomas supernatants.

Antibodies from the clusters are tested for specificity to Giardia or Cryptosporidium antigens. Clones are generated from the clusters by limiting dilution followed by screening using an immunofluorescent assay. Clones generating desired antibodies are selected, expanded and cultured. Antibodies of the desired specificity deriving from clones are then tested for isotype, and isolated in quantity from the cultures.

Water samples of approximately 100 liters of river water with a measured turbidity of ~3 nephelometric turbidity units (NTU) were concentrated using a vortex flow assembly (Membrex, Inc., Fairfield, N.J., USA). A hydrophilic, polymeric membrane of 500,000 Da molecular weight cutoff of approximately 0.05 micrometer pore size (Membrex, Inc., Fairfield, N.J.), was used at a rotational speed of 4,000 rpm. The system configuration provided 0 to 15 pounds per square inch of pressure from a water source with a permeate negative pressure of minus 5 to 12 pounds per square inch. In this configuration the membrane exhibited a membrane flux rate of 40 to 150 millimeters per minute. The 100 liter samples were processed and the retentate removed when the volume approached 5 to 15 ml. The retentate was placed in a test tube.

Two milliliters of retentate was placed in a separate test tube and $1.6 \times 10^3$ Cryptosporidium oocysts were added to the retentate. Cesium chloride was added from a concentrated liquid stock solution to 0.54 g/ml including 25 mM Tris pH 7.28 and 10 mM EDTA. This sample was applied to a three part gradient of CsCl in the following ratio of 7.5 ml each (top to bottom); 1.4 g/ml:1.1 g/ml:1.05 g/ml contained in a 36 ml (25×88 mm) PET "polyclear" ultracentrifuge tube (DuPont-Sorvall, Wilmington, De.). The gradient was centrifuged at 16,000×g for 1 hour at 4° C. in a swinging bucket rotor (SW 27, Beckman Instruments, Fullerton Calif.) in a Beckman L3-40 ultracentrifuge. The top 10 ml was discarded and the middle ~25 ml of the gradient was removed, leaving the bottom pellet. This middle layer was further processed by dilution to 150 ml with phosphate buffered saline (PBS), placed back in the vortex flow assembly, and concentrated to ~15 ml, at which time the concentration was stopped and 150 ml of water was added again to the chamber, and the diluted sample was reconcentrated to 15 ml. This retentate was removed, placed in a 50 ml conical centrifuge tube and centrifuged at 2000×g for 15 min., and resuspended to 500µl.

Cryptosporidium-specific monoclonal antibodies (Crypt-a-Glo, Waterborne Inc, New Orleans, La.; cat # A400-UN) were added to the test tube at a concentration of 4µg/ml and allowed to incubate for 30 minutes at room temperature with agitation. Twenty microliters of fluorescein isothiocyanate labeled goat anti-mouse IgM (Kirkegaard and Perry Labs, Gaithersburg, Md.) was added to the mixture and incubated for 30 min. at room temperature with agitation. After centrifugation and removal of the unbound antibodies, the oocysts were then resuspended in 100 µl and examined by epifluorescence microscopy. Seventy five percent (75%) of the input oocysts were recovered. This result validated the use of density gradient separations in conjunction with vortex flow filtration for the recovery of Cryptosporidium oocysts from surface water.

Thus, the present invention provides practical means for the detection of Cryptosporidium oocysts and Giardia cysts.

While preferred embodiments have been illustrated and described, it is understood that the present invention is capable of variation and modification and, therefore, should not be limited to the precise details set forth but should include such changes and alterations that are within the purview of the following claims.

We claim:

1. A method for detecting an organism selected from the group consisting of Cryptosporidium oocysts and Giardia cysts, in a water sample having an initial sample volumes comprising the steps of:

a) concentrating the sample by a factor of $1\times10^2$ to $1\times10^5$ of the initial volume by removing and discarding water to form a retentate;

b) applying the retentate to a density gradient, said density gradient allowing debris and the selected organisms present in the retentate to migrate through the density gradient at different rates;

c) applying a gravitational field sufficient to cause migration of debris through said density gradient to form at least one layer which retains the selected organisms and non-organism containing fractions; and d) separating said layer from the non-organism containing layers and determining the presence of the selected organisms.

2. The method of claim 1 wherein said step of concentrating said sample is performed with a polymeric membrane.

3. The method of claim 2 wherein said membrane has a molecular weight cut off of 100,000–500,000 Da.

4. The method of claim 2 wherein said membrane has a pore size of 0.01–0.05 μm.

5. The method of claim 1 wherein said step of concentrating the sample is performed with vortex flow.

6. The method of claim 1 wherein said density gradient is formed using cesium chloride.

7. A kit for detecting an organism selected from the group consisting of Cryptosporidium oocysts and Giardia cysts in a water sample having an initial volume, said kit comprising:

a) a concentrating means to concentrate the water sample by a factor of $1\times10^2$ to $1\times10^5$ of the initial volume by removing and discarding water to form a retentate;

b) a density gradient means for receiving said retentate, said density gradient means allowing debris present in said retentate to migrate through said density gradient means and said density gradient means retaining one or more of the selected organisms in a layer following application of a gravitational field; and c) a detecting means for detecting the presence of the one or more said selected organisms in said layer.

8. The method of claim 1 wherein the density gradient is formed with a salt and said salt is removed prior to the determination of the presence of said organisms in step d).

* * * * *

UNITED STATES PATENT AND TRADEMARK OFFICE
CERTIFICATE OF CORRECTION

PATENT NO. : 5,789,190
DATED : August 4, 1998
INVENTOR(S) : Joseph H. Crabb and Nathan B. Turner It is certified that error appears in the above-indentified patent and that said Letters Patent is hereby corrected as shown below:

In Claim 1, line 3, delete "volumes" and substitute therefor ---volume,---.

In Claim 1, line 17, delete "layers" and substitute therefor ---fractions---.

Signed and Sealed this

Twenty-fourth Day of November,1998

Attest:

BRUCE LEHMAN

*Attesting Officer*  *Commissioner of Patents and Trademarks*